(12) United States Patent
Yacoby-Zeevi

(10) Patent No.: US 6,423,312 B1
(45) Date of Patent: *Jul. 23, 2002

(54) COMPOSITIONS INCLUDING GLYCOSAMINOGLYCANS DEGRADING ENZYMES AND USE OF SAME AGAINST SURFACE PROTECTED BACTERIA

(75) Inventor: Oron Yacoby-Zeevi, Meitar (IL)

(73) Assignee: Insight Strategy & Marketing Ltd., Rehovot (IL)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/140,888

(22) Filed: Aug. 27, 1998

Related U.S. Application Data (63) Continuation-in-part of application No. 09/046,475, filed on Mar. 25, 1998, now Pat. No. 6,153,187, which is a continuation-in-part of application No. 08/922,170, filed on Sep. 2, 1997, now Pat. No. 5,968,822.

(51) Int. Cl.$^7$ ................................................ A61K 38/51
(52) U.S. Cl. .................. 424/94.5; 424/94.1; 424/94.61; 424/94.62; 435/183; 435/200; 435/209; 435/252.1
(58) Field of Search .............................. 435/252.1, 183, 435/200, 232; 424/94.1, 94.5, 94.61, 94.62

(56) References Cited

FOREIGN PATENT DOCUMENTS

| | | |
|---|---|---|
| JP | 06197760 | 7/1994 |
| JP | 09009962 A | 1/1997 |

OTHER PUBLICATIONS

S.A. Anatolil "Hyaluronic capsule as one of the factors of hemolytic Streptococcus pathogenicity", Chem. Abstracts. 86(17): 339, Abstr. 118714 citing Zh. Mikrobiol. Epidemiol. Immunobiol. 1977 (2): 22–27, Apr 1977.*
M.R Wessels et al., "effects of Virulence of Mutations in a Locus Essential for Hyaluronic Acid Capsule Expression in Group A Streptococci", Infect. Immun. 82(2): 433–441, Apr. 1977.*
R.A. Hatch et al., "Alginate Lyase Promotes Diffusion of Aminoglycosides Through The Extracellular Polysaccharide of Mucoid *Psuedomonas aeruginosa*", Antimicrob. Agents Chemother. 42(4): 974–977, Apr. 1998.*
I.W. Sutherland. "Sturture–Function Relationships in Microbial Exopolysaccharides", Biotech. Adv. 12: 393–448, 1994.*
"Handbook of Microbiology", vol. 1, 1974, pp 239–242, article by Clancy, C.F.
"*Pseudomonas*: biotransformations, pathogenesis, and evolving biotechnology", Eds. Silver etal, American Society for Micribiology, 1990, Chps 2, 3.

Wang et al. "Isolation and Characterization of *Pseudomonas Aeruginosa* Genes Inducible by Respiratory Mucus Derived from Cystic Fibrosis Patients", *Mol. Microbiol*, 22(5): 1005–1012, 1996 (Abstract).
Moss et al, "Reduced IL–10 Secretion by CD4+T Lymphocytes Expressing Mutant Cystic Fibrosis Transmembrane Conductance Regulator (CFTR)", *Clin Exp. Immunol.,* 106(2):374–388, 1996 (Abstract).
Davies et al, "Regulation of the Alginate Biosynthesis Gene algC in *Pseudomons Aeruginos* During Biofilm Development in Continuous Culture", *Appl. Environ. Microbiol.,* 61(3): 860–867, 1995 (Abstract).
Azghani et al, "A Beta–linked Mannan Inhibits Adherence of *Pseudomonas Aeruginosa* Human Lung Epithelial Cells", *Glycobiology,* 5(1): 39–44, 1995, (Absract).
Ofek et al, "Bacterial Adhesion to Cells and Tissues", Chapman & Hall, New York 1994, pp 114–118, 148–153, 418–423.
Davies et al, "The Involvement of Cell–to–Cell Signals in the Development of a Bacterial Biofilm", *Science* 280: 295–298, 1998.
Ghani et al, "Ceftazidime, Gentamicin, and Rifampicin, in Combination, Kill Biofilms of Mucoid *Pseudomonas Aeruginosa*", *Can. J. Microbiol,* 43(11): 999–1004, 1997 (Abstract).
Stickler et al, An Assessment of the Ability of a Silver–Releasing Device to Prevent Bacterial Contamination of Urethral Catheter Drainage Systems, *British J. Urology,* 78: 579–588, 1996.
Potera, C., "Bacteria in Biofilms Exchange Developmental Signals", *ASM News*, 64(6): 321–322 (1998).
Gabriel et al, "In Vitro Adherence of *Pseudomonas Aeruginosa* to Four Intraocular Lenses", *J. Catatact Refract. Surg.* 24:124–129, 1998.
Pier, G.B., "Rationale for Development of Immunotherapies that Target Mucoid *Pseudomonas Aeruginosa* Infriction in Cystic Fibrosis Patients", *Behring Inst Mitt,* 98:350–360, 1997 (Abstract).
Hatano et al, "Biologic Activities of Antiobodies to the Neutral–Polysaccharide Component of the *Pseudomonas Aeruginosa* lipopolysaccharide are Blocked by O Side Chains and Mucoid Exopolysaccharide (Alginate)", *Infect Immun,* 63(1):21–26 (Abstract).
Meluleni et al, "Mucoid *Pseudomonas Aeruginosa* Growing in a Biofilm in vitro are killed by Opsonic Antibodies to the Mucoid Exopolysaccharide Capsule but not by Antibodoes Produced During Chtonic Lung Infection in Cystic Fibrosis Patients", *J. Immun,* 155(4):2029–2038, 1995 (Abstract).

(List continued on next page.)

*Primary Examiner*—Rebecca E. Prout
(74) *Attorney, Agent, or Firm*—G.E. Ehrlich Ltd.

(57) ABSTRACT

A method of rendering a surface protected bacteria more susceptible to an anti-bacterial agent effected by subjecting the bacteria to a glycosaminoglycans degrading enzyme.

1 Claim, 7 Drawing Sheets

(7 of 7 Drawing Sheet(s) Filed in Color)

OTHER PUBLICATIONS

Venet et al, "Virulence Factors (aerobactin and mucois phenotype) in Klebsiella Pneumoniae and *Escherichia coli* Blood Culture Isolates", *FEMS Microbiol Lett*, 130 (1): 51–57, 1995 (Abstract).

Pier et al, "How Mutant CFTR May Contribute to *Pseudomonas Aeruginosa* Infection in Cystic Fibrosis", *Am J Respir Crit Care Med*, 154(4): S175–S182, 1996 (Abstract).

Pier et al, "Cystic Fibrosis Transmembrane Conductance Regulator is an Epithelial Cell Receptor for Clearance of *Pseudomonas Aeruginosa* from the Lung", *Proc Natl Acad Sci USA*, 94(22): 12088–93, 1997 (Abstract).

Boucher et al, "Mucoid *Pseudomonas Aeruginosa* in Cystic Fibrosis: Characterization of Mue Mutations in Clinical Isolates and Analysis of Clearance in a Mouse Model of Respiratory Infection", (Abstract) no further information given.

Boucher et al, "Two Distinct Loci Affecting Conversion to Mucoidy *Pseudomonas Aeruginosa* in Cystic Fibrosis Encode Homologs of the Serine Protease HtrA", *J. Bacteriol*, 178(2):511–523, 1996 )Abstract).

Yu et al, "Microbial Pathogenesis in Cystic Fibrosis: Pulmonary Clearance of Mucoid *Pseudomonas Aeruginosa* and Inflamation in a Mouse Model of Repeated Respiratory Challenge", *Infection and Immunity*, 66(1): 280–288, 1998.

Van Heeckeren et al, "Excessive Inflamatory Response of Cystic Fibrosis Mice to Bronchopulmonary Infection with *Pseudomonas Aeruginosa*", *J. Clin Invest*, 100(11): 2810–2815, 1997.

Mrsny et al, "Addition of a Bacterial Alginate Lyase to Purulent CF Sputum in vitro can Result in the Disruption of Alginate and Modification of Sputum Viscoelasticity", *Pul Pharmacol*, 7(6): 357–366, 1994 (Abstract).

Wiils et al, "Short–Term Recombinant Human Dnase in Bronchiectasis. Effect on Clinical State and in vitro Sputum Transportability", (Abstract) no further information.

Cai et al, "Comparison of Sputum Processing Techniques in Cystic Fibrosis", *Pediatr Pulmonol*, 22(6):402–407, 1996 (Abstract).

R.J. Mrsny et al, "Distribution of DNA and Alginate in Purulent Cystic Fibrosis Sputum: Implications to Pulmonary Targeting Strategies", *J. Drug Therapy*, 4(4): 233–243, 1996.

Hatch et al, "Alginate Lyase Promotes Diffusion of Aminoglycosides Through the Extracellular polysaccharide of Mucoid *Pseudomonas Aeruginosa*", *Antimicrob Agents Chemother*, 42(4): 974–977, 1998 (Abstract).

Speert et al, "Modulation of Macrophage Function for Defense of the Lung against *Pseudomonas Aeruginosa*", *Behring Inst Mitt*, 98: 274–282, 1997 (Abstract).

Ying et al, "Alginate, the slime Exopolysacharide of *Pseudomonas Aeruginosa*, Binds Human Leukocyte Elastase, Retards Inhibition by Alpha 1–proteinase Inhibitor, and Accelerates Inhibition by Secretory Leukoprotease Inhibitor", *Am J Cell Moll Biol*, 15(2): 283–291, 1996 (Abstract).

Johansen et al, Chronie *Pseudomonas Aeruginosa* Pneumonia, A New Prophylactic Principle, *Behring Inst Mitt*, 90: 269–273 1997 (Abstract).

Pina et al, "The Role of Fluoroquinolones in the Promotion of Alginate Synthesis and Antibiotic Resistance in *Pseudomonas Aeruginosa*", *Curr Microbiol*, 35(2): 103–108, 1997 (Abstract).

Spencer, RC, "Invasive Streptococci", *Eur J Clin Microbiol Infest Dis*, 14 Suppl 1:S26–S32, 1995 (Abstract).

Mengistu et al, "Continuous Culture Studies on the Synthesis of Capsular Polysaccharide by *Klebsiella Pneumoniae* K1", *J Appl Bacteriol*, 76(5): 424–430, 1994 (Abstract).

Hsuch et al, "Invasive *Streptococci Pneumoniae* Infection Associated with Rapidly Fatal Outcome in Taiwan", *J Formos Med Assoc*, 95(5):364–371, 1996 (Abstract).

Moses et al, "Relative Contributions of Hyaluronic Capsule and M Protein to Virulence in a Mucoid Strain of the Group A Streptococcus", *Infect Immun*, 65(1):64–71, 1997 (Abstract).

Scott et al, Visualization of an Extracellular Mucoid Layer of *Treponema Denticola* ATCC 35405 and Surface Sugar Lectin Analysis of Some Treponema Species, *Oral Microbiol Immunol*, 12(2): 121–125, 1997 (Abstract).

Nilsson et al, "The Role of Staphylococcal Polysaccharide Microcapsule Expression in Septricemia and Septic Arthritis", *Infect Immun*, 65(10): 4216–21, 1997 (Abstract).

Wessels et al, "Effects on Virulence of Mutations in a Locus Essential for Hyaluronic Acid Capsule Expression in Group A Streptococci", *Infect Immun*, 62(2): 433–441, 1994 (Abstract).

* cited by examiner

COMPOSITIONS INCLUDING GLYCOSAMINOGLYCANS DEGRADING ENZYMES AND USE OF SAME AGAINST SURFACE PROTECTED BACTERIA

This is a continuation, in part of U.S. patent application Ser. No. 09/046,475, filed Mar. 25, 1998 now U.S. Pat. No. 6,153,187, which is a continuation-in-part of U.S. patent application Ser. No. 08/922,170, filed Sep. 2, 1997 now U.S. Pat. No. 5,968,822.

FIELD AND BACKGROUND OF THE INVENTION

The present invention relates to the use of glycosaminoglycans degrading enzymes, such as, but not limited to, heparanases, connective tissue activating peptide III (CTAP), heparinases, hyaluronidases and chondroitinases, against surface protected bacteria, for reduction of bacterial alginate and for the disruption of bacterial biofilms. More particularly, the present invention relates to the use of glycosaminoglycans degrading enzymes for treating conditions resulting from infection by mucoid, alginate-producing and/or biofilm-producing bacteria.

Glycosaminoglycans degrading enzymes: Glycosaminoglycans (GAG) are unbranched polyanionic polysaccharides made up of repeating disaccharides. One component of which is always an amino sugar. Degradation of GAG is carried out by a battery of lysosomal hydrolases. These include certain endoglycosidases (heparanse and CTAP degrade heparan sulfate and to a lesser extent heparin, and hyaluronidase from sheep or bovine testes degrade hyaluronic acid and chondroitin sulfate), various exoglycosidases ($\beta$-glucoronidase), and sulfatases (iduronate sulfatase), generally acting in sequence to degrade the various GAG. Bacterial lyases such as heparinase I, II and III from *Flavobacterium heparinum* cleave heparin-like molecules, chondroitinase ABC from *Proteus vulgaris*, AC from *Arthrobacter aurescens* or *Flavobacterium heparinum*, B and C from *Flavobacterium heparinum* degrade chondroitin sulfate.

Bergey's Manual of Determinative Bacteriology describes 149 species of the genus Pseudomonas. However as with species designations in other groups of organisms, many are based on minor points of difference, which may vary under different conditions of growth and nutrition. Most species are motile with polar flagella: straight rods or occasionally coccoid in shape. They grow well on conventional culture media, and many strains thereof produce characteristic pigmentation. All species except *P. maltophilia* are recognized as having a cytochrome C oxidase present when tested with tetramethyl-p-phenylenediamine, a characteristic that distinguishes them from the enterobacteroaceae. Although Pseudomonas are not particularly invasive, once they are established as infective agents, they are very difficult to eradicate (Handbook of Microbiology, Vol. 1 1974 pp. 239–242).

*Pseudomonas aeruginosa* is an opportunistic pathogen responsible for a wide range of infections, one of the most debilitating being chronic pulmonary infection in cystic fibrosis (CF) patients. The basic alteration in the bronchial/pulmonary environment of the CF lung causing increased secretion of hyperviscous mucus favors bacterial colonization by *Staphylococcus aureus, Haemophilus influenzae* and *P. aeruginosa*. Prolonged antibiotic therapy and the increasing life expectancy of CF patients may influence the prevalence of all of these organisms in the lung flora. *P. aeruginosa* is found in patients with moderate and severe pulmonary disease, being the sole pathogen found in sputum in the most advanced stages of the disease. *P. aeruginsosa* is particularly resistant to even the most aggressive chemotherapy and has been found to colonize the lungs of 50–90% of all CF patients. It has been shown that the severity of lung infection in CF patients is directly correlated to the presence of mucoid strains. The mucoid *P. aeruginosa* isolates revert at a high frequency to a nonmucoid form upon serial transfers in the laboratory.

The pathogenicity of mucoid *P. aeruginosa* in the CF lung is attributed in part to the synthesis of the exopolysaccharide alginate by the bacterium. Nonmucoid strains of *P. aeruginosa* initially colonize the upper respiratory tract of CF patients. However, mucoid alginate-producing variants appear with prolonged infection and eventually predominate in the CF lung. The alginate produced by these mucoid strains of *P. aeuriginosa* compounds the problems related to the hyperviscous bronchial secretions of CF patients. Alginate-producing strains of *P. aeruginosa* are almost exclusively associated with respiratory tract infections that accompany CF. Although 80% of the *P. aeruginosa* isolates form CF patients are mucoid, only about 1% of clinical *P. aeruginosa* isolates from other types of infections are mucoid. Alginate appears to protect *P. aeruginasa* by shielding it from host immune defense and antibiotic therapy, and possibly enables it to adhere more effectively to respiratory tract tissues. Once established in the CF lung, these mucoid strains tend to persist and parallel the progressive clinical deterioration of the patient. Alginate is a linear acetylated copolymer consisting of $\beta$-1,4-linked D-mannuronic acid and variable amounts of its C-5 epimer L-guluronic acid. Alginate is produced by several bacterial species, the most widely known being *Azotobacter vinelandii* and *P. aeruginosa*. Bacterial alginates differ from algal alginate in that the former contain O-acetyl groups. The viscosity level of alginate may play a role in the pathogenesis of mucoid *P. aeruginosa* in the CF respiratory tract. Several enzymes are involved in the alginate biosynthetic pathway: Phosphomannose isomerase (PMI), GDP-mannose dehydrogenase (GMD), and GDP-mannose pyrophosphorylase (GMP) in mucoid, alginate-producing *P. aeruginose*. Activities of the enzymes are either absent or greatly reduced in nonmucoid strains.

Alginate synthesis by the highly mucoid *P. aeruginosa* 8821 M is growth-phase-dependent and the alginate produced per unit of biomass reaches maximum values in the deceleration phase of growth. However, the degree of polymerization increases as batch growth proceeds, reaching maximum values at the stationary phase of growth (Leitao J H, Sa-Correia I; Arch Microbiol 1995, March; 163(3): 217–222).

Regulation of alginate synthesis: The regulation of alginate biosynthesis by *P. aeruginosa* appears to involve fine tuning of several factors. A pivotal step in alginate biosynthesis is the activation of the algD gene in mucoid, alginate-producing *P. aeruginosa*. algD is highly activated in response to increased concentrations of either KCl or NaCl. This is an interesting finding since the CF lung is rich in Na$^+$, Cl$^-$ and K$^+$ ions.

Alginate-producing strains of three other Pseudomonas species (*P. fluorescens, P. putida,* and *P. mendocina*) have been isolated in vitro by growth on subinhibitory concentrations of carbenicillin. Also, certain phytopathogen Pseudomonas species produce alginate both in planta and in vitro. These observations suggest that many species of Pseudomonas harbor genes involved in alginate biosynthesis, but that they are not normally expressed. Since many of the *P. aeruginosa* alginate genes had been cloned, it was possible to examine genomic DNA from various Pseudomonas species and phylogenetically related organisms for sequences homologous to the *P. aeruginosa* alg genes. Southern hybridization studies using algA, pmm, algD, and algR1 as probes showed some degree of homology with several Pseudomonas species belonging to Pseudomonas RNA homology group 1. Some probes also hybridized with Azotobacter, Azomonas, and Serpens species. In the laboratory, the alginate-producing (alg+) phenotype is somewhat unstable, and nonmucoid (alg−) revertants are commonly seen. Genetic mapping experiments have shown that the switching between alg+ and alg− is due to a genetic change in one region of the chromosome located at about 68 min on the 75-min chromosomal linkage map of Pseudomonas. This was originally referred to as the muc locus. Two additional recognized genes are involved in the regulation of alginate production. These are algR at 9 min and algB at 13 min, both of which are required for high-level alginate production. However, most of the alginate biosynthetic genes appear to be located in a larger gene cluster at 34 min.

Collectively, the regulation of the alginate biosynthetic pathway in *P. aeruginosa* is multigenic and appears to be relatively complex, which suggests that this system has a long evolutionary history. Alginate is secreted in copious amounts (e.g., 2 mg/ml in culture supernatants), thus channeling much of the available carbon and energy sources toward its production. It is not surprising that alginate biosynthesis would be tightly regulated. However, when production of alginate is advantageous to the organism (such as in the CF respiratory tract) the rare mucoid cells in the population become predominant because of their selective advantage. When alginate production is no longer advantageous, the instability of the Alg+ phenotype (controlled by the genetic switch algS) allows the nonmucoid population to quickly become predominant as a result of the ability to conserve carbon and energy resources. Environmental factors may also play a role in the frequency of alginate conversion. Because virtually all CF isolates of *P. aeruginosa* are mucoid, it was postulated that the lung environment of CF patients provides the trigger required to turn on the production of the alginate adhesin. To identify virulence genes of *P. aeruginosa* that are important in infection of CF patients, an in vivo selection system (IVST) was used to identify promoters that are specifically inducible by respiratory mucus derived from CF patients. Three genetic loci that are highly inducible by the mucus were identified (Wang J et al.; Mol Microbiol 1996 December; 22(5): 1005–12).

It is unlikely that this complex regulatory scheme to activate alginate production evolved solely as a pathogenic mechanism specific for the infection of CF patients. *P. aeruginosa* normally dwells in the soil environment, and alginate conversion may have evolved to protect the bacterial population from destruction due to attack by bacteriophages or bactriocins or from desiccate during periods of dryness. However, *P. aeruginosa* is a remarkable opportunistic pathogen and has adapted the alginate conversion system to promote debilitating and life threatening pulmonary infections of CF patients. Understanding alginate gene regulation in *P. aeruginosa* may lead to treatments that could turn off alginate production by the organisms resident in the CF lung, thus improving the longevity and quality of life for these patients (Pseudomonas: biotransformations, pathogenesis, and evolving biotechnology. Edited by Simon Silver et al., 1990 Am. Soc. For Microbiol. Ch. 2 and 3, pp. 15–36)

Adhesion mechanisms of *P. aeruginosa*: Adherence through carbohydrate-binding adhesins is an early step in colonization of the lung by gram-negative organisms (Azghani AO et al.; Glycobiology 1995, February; 5(1): 39–44). *Pseudomonas aeruginosa* is an opportunistic pathogen capable of causing serious localized infections of the cerebrospinal fluid (CSF), urinary tract, eye, ear, lung, skin, and other parts of the body. The organism is often isolated from peritoneal dialysis membranes. Generalized systemic infections tend to occur only in injured, immunodeficient, or otherwise compromised patients. It is not surprising, therefore, that this genus has developed a number of adhesion mechanisms, each being specific for a particular type of substratum. There are numerous articles reporting various mechanisms of adhesion for *P. aeruginosa*. These include the hydrophobic effect, adhesion to and by alginates, and lectin-dependent adhesion. Some reports maintain that the adhesion of *P. aeruginosa* is fimbriae-dependent. The exopolysaccharide alginate binds to buccal epithelial and tracheal cells, as well as to bronchotracheal mucin. Antipolysaccharide inhibits binding of the organisms to the tracheal cells. Also, mucoid strains of Pseudomonas adhere much better to tracheal cells compared to nonmucoid strains or compared to alginate-producing bacteria grown in an antibiotic medium to reduce alginate production. Alginate appears to play a role in the adhesion of Pseudomonas to contact lenses. Microscopic evidence suggests that mucoid strains may adhere to ciliated tracheal cells and to inert surfaces, including contact lenses, by polysaccharide-like materials. The presence of alginate in the reaction mixture causes an increase in the number of bacteria adherent to tracheal cells or immobilized mucin. It has been suggested that the alginate may act to trap and tether the organisms to the substrata, thereby allowing other adhesins, such as the fimbrial adhesin complex, to bind the specific receptors. If the target animal cell or substrata lacks the ability to bind alginate, then the presence of an exopolysaccharide coat on the bacterial surface may actually impede the ability of the organisms to attach to such animal cells. This may explain the rescued ability of the mucoid strains to bind to phagocytic cells or to primary cultures of cilliated epithelial cells. The phagocytic cells lack the ability to bind alginate.

There are several reports showing that adhesion of *P. aeruginosa* to various substrata may involve lectins specific for carbohydrates other than sialic acid. For example, adhesion of the bacteria to the tracheal epithelium is inhibited by D-galactose and N-acetyl-D-glucosamine. Moreover, putative nonfimbrial adhesins produced by both mucoid and nonmucoid strains of Pseudomonas, specific for Galβ1, 4GlcNAc or Galβ1, 3GlcNAc sequences, may be involved in mediating binding of the organisms to human bronchial mucins (Bacterial Adhesion to Cells and Tissues/Ofek I and Doyle R J, 1994 Chapman & Hall, Inc. pp. 114–116, 418–421).

*P. aeruginosa* biofilms: Bacteria in nature often exist as sessile communities called biofilms. These communities develop structures that are morphologically and physiologically differentiated from free living bacteria. A cell-to-cell signal is involved in the development of *P. aeruginosa* biofilms. The involvement of an intercellular signal molecule in the development of *P. aeruginosa* biofilms suggests possible targets to control biofilm growth on catheters, in CF and in other environments where *P. aerugiosa* biofilms are a persistent problem. Biofilms of *P. aeruginosa* develop on solid surfaces exposed to a continuous flow of nutrients. The biofilm structures consist primarily of an exopolysaccharide matrix or glycocalyx in which the bacteria are embedded.

Cell to cell signal is required for the differentiation of individual cells of the common bacterium P. aeruginosa into complex multicellular structures. P. aeruginosa cells in biofilms secrete a particular homoserine lactone, 3-oxododecanoylhomoserine (OdDHL), that helps to control biofilm differentiation. OdDHL binds an R-protein inside the target cell, activating RNA polymerases that are involved in forming the biofilm. A mutation that blocks generation of the signal molecule hinders differentiation, and the resulting abnormal biofilm appears to be sensitive to the detergent biocide SDS. The control of biofilm differentiation and integrity by quorum sensing has important implications in medicine. Because of their innate resistance to antibiotics and other biocides, biofilms in these environments are difficult, if not impossible, to eradicate. Bacterial biofilms also present other problems of significant economic importance in both industry and medicine. The finding of a connection between biofilm differentiation into clusters of bacteria resistant to the detergent biocide SDS and a quorum-sensing signal suggests that inhibition of these cell-to-cell signals could aid in the treatment of biofilms (Davies D G et al.; Science vol 280 Apr. 10, 1998).

It was shown that in continuous flow biofilm cultures in medium resembling CF bronchial secretions, P. aeruginosa was not eradicated form biofilms by 1 week of treatment with high concentrations of ceftazidime and gentamicin, to which they are sensitive on conventional testing. The addition of rifampicin, which has little activity against the strains as measured by the minimum inhibitory concentration, led to the apparent elimination of the bacteria from the biofilms. The effect was not strain specific. Ghani M and Soothill J S; Can J microbiol 1997, November; 43(11): 999–1004.

Scanning electron microscopy (SEM) showed that the internal surfaces of catheters and drainage systems are commonly colonized by thick layers or biofilms of organisms embedded in a polysaccharide matrix. There is evidence from laboratory and clinical studies that the progressive spread of the biofilm along the luminal surfaces of the bag, tube and catheter leads to bladder infection (Stickler D J et al.; Br J Urol. 1996, 78; 579–88).

Biofilms are also an integral part of dental plaque, thereby contributing to tooth decay and periodontal disease. One target is *Fusobacterium nucleatum*, an oral bacteria found in biofilms coating the area between teeth and gums (Potera C; ASM News, 64(6), 1998).

The incidence of gram-negative bacteria in reviews of postoperative acute endophthalmitis ranges from 3–22% with P. aeruginosa being one of the more common etiological agents of fulminant infections. These infections usually develop within days of the surgery and have a poor prognosis. P. aeruginosa has been reported to adhere to damaged corneal cells as well as to contact lenses. Its adherence to silicone and latex materials is significantly greater that of several isolates of Staph. Epidermidis. The in vitro adherence of P. aeruginosa to a variety of hydrogel and rigid gas-permeable contact lenses correlates with clinical data. P. aeruginosa adheres to the optic material of intraoccular lenses: AcrySof-acrylic<PMMA<silicone1<silicon2, and form biofilms (Manal M et al.; J Cataract Refract Surg vol. 24, January 1998).

CF lung predilection for excessive inflammation and infection with P. aeruginosa: In CF, defective function of the CFTR in airway epithelial cells and submucosal glands, results in chronic pulmonary infection with P. aeruginosa. The pulmonary infection incites an intense host inflammatory response, causing progressive suppurative pulmonary disease. Several hypotheses have been proposed to explain CF lung predilection for excessive inflammation and infection with P. aeruginosa.

The role of alginate in pathogenesis is complex and appears to confer antiphagocytic properties and an adherence mechanism upon the organism. Autopsies show that mucoid P. aeruginosa forms adherent microcolonies in the lung. Alginate does not firmly adhere to the organisms but is released in large quantities into the respiratory environment. Because alginate is very viscous in aqueous solution, it probably contributes to the high viscosity of the bronchial secretions in the CF lung, resulting in obstruction of small airways, interference with mucociliary airway clearance, and impaired movement to phagocytes. The mucoid organisms may be more adapted to a chronic infection because they secrete lower levels of proteases, which would otherwise cause extensive lung damage and acute infection. Also P. aeuruginosa can utilize the respiratory secretions of the CF lung to support rapid growth and alginate biosynthesis; thus, the mucus-congested CF respiratory tract provides P. aeruginosa with a nutritionally rich environment favorable to clonization. The initial colonization of the CF upper respiratory tract appears to be with a nonmucoid strain and is often asympomatic. This usually precedes the emergence of mucoid variants of the original strain and is followed by chronic infection and a poor prognosis for the patient.

CF patients do produce opsonic antibodies to mucoid P. aeruginosa that are in a planktonic or suspended state, but these antibodies fail to kill P. aeruginosa growing in a biofilm (Pier G B; Behring Inst Mitt 1997 February; 98: 350–60). Results showed that alginate and neutral polysaccharides are involved in phagocytic impairment of P. aeruginosa (Pasquier C et al.; FEMS Microbiol Lett 1997 February 15; 147(2): 195–202). Alginate production inhibits opsonic and nonopsonic phagocytosis, protects cells form reactive oxygen intermediates and plays additional roles associated with biofilm phenomena (Hatano K et al.; Infect Immun. 1995, January; 63(1): 21–26; Meluleni G J et al.; J. Immunol. 1995, August 15; 155(4): 2029–38). The results support the findings of the previous extensive work carried out in vitro, suggesting that the phagocytic and other bactericidal systems in the lung are impaired: Some investigators suggest that the elevated salt content in the surface fluid of the CF airway renders human β-defensin-1 nonfunctional, eliminating the bactericidal activity of the respiratory epithelium. Another hypothesis suggests that failure of the respiratory epithelial cells in the CF lung to ingest bacteria and be sloughed allows for P. aeruginosa retention at the endobronchial surface. The airway epithelial cell ingestion of bacteria followed by cellular desquamation may protect the lung from infection, and epithelial cells expressing mutant forms of the CFTR may be defective in this function. It was found that transformed human airway epithelial cells homozygous for the delta F508 allele of CFTR were significantly defective in uptake of P. aeruginosa compared with the same cell line complemented with the wild-type allele of CFTR. Defective epithelial cell internalization of P. aeruginosa may be a critical factor in hyper susceptibility of CF patients to chronic lung infections (Pier G B et al.; Am J Respir Crit Care Med 1996 October; 154(4 Pt 2): S175–82; Proc Natl Acad Sci USA 1997 October 28; 94(22): 12088–93). The majority of CF mucoid isolates carry mucA mutations which allow transcription of alginate biosynthetic genes, resulting in a mucoid phenotype. Mucoidy is caused by muc mutations that depress the alternative sigma factor encoded by algU, which in turn activates alginate biosynthetic and ancillary regulatory genes (Boucher J C et al.; Infec Immun 1997 September; 65: 3838–46; Boucher J C et al.; J Bacteriol 1996 January; 178(2): 511–23). Mucoid cells are cleared less efficiently and appears to linger in the lung longer that nonmucoid organisms. This finding suggests that mucoidy may confer an ability to resist innate clearance mechanisms in the lung and, along with other potentially contributing factors, could be the basis for selection of mucA mutants in CF (Yu H et al.; Infec and Immun. 1998, 66(1): 280–88). Another possibility is that Pseudomonas adheres to epithelial cells in the CF airway in greater numbers because of the abnormal surface properties of the cells, thus leading to infection.

Although details of the mechanism differ, all of these hypotheses predict that the basic defect in CF permits retention of bacteria at an otherwise sterile site, providing the stimulus for inflammation. Furthermore, it is suggested that the CF genotype is associated with excessive inflammatory response compared with the normal response, even if the initiating stimulus is similar. In order to understand the pathogenesis of pulmonary disease characteristic of CF, it is required to examine not only the impaired clearance of the bacteria, but also the excessive host response to P. aeruginosa (Van Heeckeren A et al.; J. Clin Inves. 1997, December; 100(11): 2810–5).

Thus, P. aeruginosa is a remarkable opportunistic pathogen and has adapted the alginate conversion system to promote debilitating and life threatening pulmonary infections of CF patients. The environment of the CF lung is unique in its capacity to induce alginate production by P. aeruginosa. However, the factors which contribute to this unusual host-pathogen interaction have not yet been determined.

Understanding alginate gene regulation in P. aeruginosa may lead to treatments that could turn off alginate production by the organisms resident in the CF lung, thus improving the longevity and quality of life for these patients. CF is the most common fatal genetic disease among the Caucasian population, affecting approximately 1:2500 newborns. The median age of survival of patients with CF has dramatically increased over the past 2 decades from less than 10 to more than 30 years. This progress has occurred primarily through improved nutritional support and aggressive management with antibiotic therapy of acute pulmonary infections. Currently there is no effective combination of therapies which completely eradicates alginate-producing P. aeruginosa from the CF lung environment. The development of new compounds effective in preventing alginate synthesis represents a major step towards reaching this goal. Such inhibitors of alginate synthesis have potential clinical applications in that elimination of the alginate capsule might render P. aeruginosa more susceptible to both antibiotic therapy and the host's immune system. Therefore, many laboratories are involved in an extensive study of the genetics and regulation of the alginate biosynthetic pathway in P. aeruginosa in an effort to identify factors unique to the CF lung environment that trigger expression of the genes involved in alginate biosynthesis and in an attempt to find nontoxic compounds that inhibit alginate synthesis by inhibiting the enzymes directly involved in the pathway.

Mrnsy R J et al. have investigated the use of an alginate lyase obtained from a bacterial source to disrupt P. aeruginosa alginate's polymeric nature and effect a change in the rheological properties of CF sputum in vitro. Their results suggested that bacterial alginate present within purulent CF sputum may be quite stable, that endogenous alginate lyase activities appear to be limited and that the in vitro addition of exogenous alginate lyase can lead to the disruption of alginate and a change in the viscoelastic properties of some purulent CF sputum samples (Mrsny R J et al.; Pulm Pharmacol 1994 December; 7(6): 357–66).

A suspension of 2% P. aeruginosa alginate completely blocked the diffusion of gentamycin and tobramycin, but not that of carbenicillin, illustrating how alginate production can help protect P. aeruginosa growing within alginate microcolonies in patients with CF from the effects of aminoglycosides. This aminoglycoside diffusion barrier was degraded with a semipurified preparation of P. aeruginosa alginate lyase (Hatch R A, Schiller N L; Antimicrob Agents Chemother. 1998, April; 42(4): 974-7).

A 41 kDa alginate lyase capable of degrading alginic acid of P. aeruginosa was prepared from the culture of Bacillus strain ATB-1015. The enzyme was found useful for the treatment of respiratory diseases caused by infection by P. aeruginosa (JP 95-181047, JP 09009962 A2 to Akira Nakagawa). Alginic acid lyase(s) which decompose alginic acid into sugar and the 4-deoxy-5-keto uronic acid is used for treatment of pulmonary cystic fibrosis (JP 06197760 A to Yakuhin Otsuka). However, these lyases fail to degrade glycosaminoglycans.

More therapeutic approaches: Phagocytosis of P. aeruginosa by macrophages is a unique two-step process; binding is glucose-independent but ingestion occurs only in the presence of D-glucose or D-mannose. Since glucose is present in only negligible quantities in the endobroncheal space, P. aeruginosa may be pathogenic by virtue of its capacity to exploit the opportunity presented in the lower airway to resist normal nonspecific phagocytic defenses. Because delivery of simple glucose by aerosol would not be effective, various approaches for targeting glucose to alvelolar macrophages by receptor-mediated endocytosis are under investigation (Speert D P et al.; Behring Inst Mitt 1997 February; 98: 274–82). The ongoing lung tissue damage in chronically P. aeruginosa infected CF patients has been shown to be caused by elastase liberated from polymorphonuclear leukocytes (PMN). Alginate alone appeared to be a weak inhibitor of the hydrolysis of long synthetic peptide substrates and [$^{14}$C]elastin by elastase. Alginate also had effects on the antielastase function of naturally occurring protease inhibitors in the lung: It reduces the association rate of elastase and alpha 1-proteinase inhibitor, whereas it increases the association rate of elastase and secretory leukoprotease inhibitor.

Based on these finding, alginate may be an important factor in determining the local distribution of leukocyte elastase and perturbing the overall protease-antiprotease balance in the infected lungs of CF patients (Ying Q L et al.; Am j Respir Cell Mol Biol. 1996, August; 15(2): 283–91).

Thus, prevention of the onset of the chronic infection or prevention of the dominance of the inflammation by PMNs would be important goals for a vaccine strategy against P. aeruginosa. Findings suggested that change from the Th2 like response seen in CF patients towards a Th1 response might improve their prognosis (Johansen H K et al.; Behring Inst Mitt 1997 February; 98: 269–73).

Care should be taken when treating nonmuoid P. aeruginosa with gyrase inhibitors such as ciprofloxacin, norfloxacin and ofloxacin, which target the A subunit of topoisomerase II, since it resulted in 100% conversion to the mucoid phenotype. An increase in resistance was observed in populations that expressed the mucoid phenotype. Both mucoid conversion and antibiotic resistance were completely reversible when ciprofloxacin pressure was withdrawn, but only partially reversible by the removal of norfloxacin and ofloxacin. Thus, these experiments indicate that in the presence of some fluoroquinolones, a conditional response resulting in mucoid conversion and antibiotic resistance may occur (Pina S E, Mattingly S J; Curr Microbiol 1997 August; 35(2): 103–8).

Other mucoid bacteria: *Klebsiella Pneumoniae* K1 synthesizes capsular polysaccharide. Non mucoid variants thereof are more susceptible to some bacteriophages, possibly due to the reduction or absence of capsular polysaccharide (Mengistu Y et al; J Appl Bacteriol 1994, May; 76(5): 424–30). There are two virulence factors of *K. pneumoniae:* aerobactin and the mucoid phenotype. Aerobactin is always associated with the mucoid phenotype (FEMS Microbiol Lett. 1995, July 15; 130(1): 51–57).

Mucoid or highly encapsulated strains of group A Streptococci have been associated both with unusually sever infections and with acute rheumatic fever. The mucoid M-type 18 strain of a group A Streptococcus has a hyaluronic acid capsule which plays an important role in virulence. The region of the chromosome essential for capsular polysaccharide expression is conserved among diverse group A streptococcal strains. Wessels M R et al.; Infec Immun 1994, February; 62(2): 433–41. In communities, where increases in cases of rheumatic fever had been reported, the serotypes M-1, 3, 5, and 18 were isolated which, on culture, produced characteristic mucoid colonies (Spencer R C; Eur J Clin Microbiol Infect Dis. 1995, 14 Suppl 1: S26–32). The mucoid serotype 3 of *S. pneumoniae* cause rapid fatal infections, despite adequate antibiotic therapy (Hsueh P R et al.; J Formaos Med Assoc 1996, May; 95(5): 364–71).

The antiphagocytic effect of M protein has been considered a critical element in virulence of the group A Streptococcus. The hyaluronic acid capsule also appeared to play an important role: studies of an acapsular mutant derived form the mucoid or highly encapsulated M protein type 18 group A strepococcal strain 282 indicated that loss of capsule expression was associated with decreased resistance to phagocytic killing and with reduced virulence in mice. The results provide further evidence that the hyaluronic acid capsule confers resistance to phagocytosis and enhances group A streptococcal virulence. Moses A E et al.; Infect Immun. 1997, January; 65(1): 64–71.

*Staphylococcus aureus* arthritis is a rapidly progressive and highly erosive disease of the joints in which both host and bacterial factors are of pathogenic importance. One potential bacterial virulence factor is the ability to express a polysaccharide capsule (CP). Among 11 reported capsular serotypes, CP type 5 (CP5) and CP8 comprise 80–85% of all clinical blood isolates. The results clearly indicated that the expression of CP5 is a determinant of the virulence of *S. aureus* in arthritis and septicemia (Nilsson I M et al.; Infec Immun 1 October; 65(10): 4216–21).

*Treponema denticola,* which has been associated with periodontitis, synthesizes or acquires and extracellular polysaccharide layer (Scott D et al.; Oral Microbiol Immunol 1997, April; 12(2): 121–5).

The above described data implies that there is a widely recognized need for, and it would be highly advantageous to have agents effective in reducing mucus production by bacteria, by, for example, degradation or prevention of synthesis of the bacterial exopolysaccharide alginate. The benefits from employing such agents for the degradation of bacterial exopolysaccharide alginate include (i) viscosity reduction of alginate related hyperviscous bronchial secretions; (ii) disruption of bacterial biofilms which may render the bacteria more susceptible to host immune defense systems and antibiotic therapy; (iii) inhibition of alginate associated adhesion to host cells and enhancement of bacterial clearance, resulting in reduction of infection rate; (vi) reduction of host's inflammatory response to infection.

SUMMARY OF THE INVENTION

According to one aspect of the present invention there is provided a method of rendering a surface protected bacteria more susceptible to an anti-bacterial agent comprising the step of subjecting the bacteria to a glycosaminoglycans degrading enzyme.

According to another aspect of the present invention there is provided a method of rendering a surface protected bacteria less capable of adhering to a substratum comprising the step of subjecting the bacteria to a glycosaminoglycans degrading enzyme.

According to yet another aspect of the present invention there is provided a method of treating a disease for relieving disease associated symptoms comprising the step of administering a therapeutical composition including a glycosaminoglycans degrading enzyme According to still another aspect of the present invention there is provided a therapeutic composition for treating a surface protected bacteria associated disease or symptoms comprising a glycosaminoglycans degrading enzyme and an antibiotic.

According to yet another aspect of the present invention there is provided a bactericide composition effective in eliminating a surface protected bacteria comprising a glycosaminoglycans degrading enzyme and a bactericide.

According to further features in preferred embodiments of the invention described below, the surface protected bacteria is a mucoid bacteria.

According to still further features in the described preferred embodiments the surface protected bacteria is an alginate-producing bacteria.

According to still further features in the described preferred embodiments the surface protected bacteria is a biofilm-producing bacteria.

According to still further features in the described preferred embodiments the anti-bacterial agent is a bactericide.

According to still further features in the described preferred embodiments the anti-bacterial agent is an antibiotic.

According to still further features in the described preferred embodiments the anti-bacterial agent is an immune moiety.

According to still further features in the described preferred embodiments the glycosaminoglycans degrading enzyme is selected from the group consisting of a lysosomal hydrolase and a bacterial lyase.

According to still further features in the described preferred embodiments the glycosaminoglycans degrading enzyme is selected from the group consisting of an endoglycosidase, an exoglycosidase and a sulfatase.

According to still further features in the described preferred embodiments the glycosaminoglycans degrading enzyme is selected from the group consisting of heparanse, connective tissue activating peptide III (CTAP), hyaluronidase, glucoronidase, iduronate sulfatase, heparinase I, heparinase II heparinase III, chondroitinase ABC, chondroitinase AC, chondroitinase B and chondroitinase C.

According to still further features in the described preferred embodiments the bacteria is of a genus selected from the group consisting of Pseudomonas, Azotobacter, Azomonas, Serpens, Fusobacterium, Klebsiella, Streptococcus, Staphylococcus and Treponema.

According to still further features in the described preferred embodiments the bacteria is of a genus Pseudomonas.

According to still further features in the described preferred embodiments the bacteria is *Pseudomonas aeruginosa*.

According to still further features in the described preferred embodiments the bacteria is in a lung of a patient suffering chronic pulmonary infection, the method being for relieving symptoms associated with the chronic pulmonary infection.

According to still further features in the described preferred embodiments the bacteria is in a lung of a cystic fibrosis patient suffering chronic pulmonary infection, the method being for relieving symptoms associated with the chronic pulmonary infection.

According to still further features in the described preferred embodiments the bacteria is growing on a non-living substratum.

According to still further features in the described preferred embodiments the non-living substratum forms a part of a medical device.

According to still further features in the described preferred embodiments the medical device is selected from the group consisting of an infusion device, a catheter device, a contact lens device, a dialysis device and a draining device.

The present invention successfully addresses the shortcomings of the presently known configurations by providing methods and compositions effective in combating surface protected bacteria (e.g., mucoid-, alginate-, biofilm-producing bacteria), by subjecting such bacteria to glycosaminoglycans degrading enzyme, rendering such bacteria surface non-protected and therefore more susceptible to anti-bacterial agents and less capable of adhering to various living and non-living substrata.

BRIEF DESCRIPTION OF THE DRAWINGS

The invention herein described, by way of example only, with reference to the accompanying drawings, wherein:

FIGS. 3a–b demonstrate the effect of heparanase on sensitivity to antibiotics. (2a) Bacteria were plated on tryptic soy agar following treatment with (from left to right, top to bottom) heparanase buffer, heparanase, boiled heparanase, chondroitinase ABC, hyaluronidase or heparinase II. Antibiotic discs were placed according to the scheme in FIG. 3b.

DESCRIPTION OF THE PREFERRED EMBODIMENTS

The present invention is of methods and compositions effective in combating mucoid, alginate-producing and/or biofilm-producing bacteria, by subjecting such bacteria to glycosaminoglycans degrading enzymes, which can be used, for example, to treat infections caused by such virulent bacteria. Specifically, the present invention can be used for the reduction of mucus production by mucoid *P. aeruginosa* and other mucus producing bacteria, disruption of bacterial biofilms, and increasing the susceptibility to antibacterial treatment, for the management of respiratory diseases including, but not limited to, cystic fibrosis, chronic bronchitis, pulmonary emphysema, infectious pneumonia, chronic obstructive lung/pulmonary disease (COLD/COPD), tuberculosis, and fungal infection, to improve clearance of lung secretions by reducing their viscoelastic properties, reduce the frequency of respiratory infections and/or inflammation requiring parenteral antibiotics and/or anti-inflammatory drugs, respectively, and to improve pulmonary function, due to degradation of mucus produced by mucus producing bacteria in general and *P. aeruginosa* in particular. It is also recommended for the treatment of infected wounds and burns, ear and eye infections, urinary tract and other catheter associated infections.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

U.S. patent application Ser. Nos. 08/922,170 and 09/109,386, which are incorporated by reference as if fully set forth herein teach the cloning of the heparanase gene. U.S. patent application Ser. No. 09/071,618, filed May 1, 1998, which is incorporated by reference as if fully set forth herein, teaches the production of recombinant heparanase by a variety of heterologous expression systems and the purification of recombinant heparanase. U.S. patent application Ser. No. 09/046,475, which is incorporated by reference as if fully set forth herein, teaches the use of glycosaminoglycans degrading enzymes for the management, treatment and relieve of symptoms of respiratory diseases associate with accumulation of mucoid, mucopurulent or purulent material containing glycosaminoglycans. The present invention, on the other hand, relates to the use of glycosaminoglycans degrading enzymes to combat mucoid-, alginate- and/or biofilm-producing bacteria.

Thus, according to one aspect of the present invention there is provided a method of rendering a surface protected bacteria more susceptible to an anti-bacterial agent. The method is effected by subjecting the surface protected bacteria to a glycosaminoglycans degrading enzyme.

According to another aspect of the present invention there is provided a method of rendering a surface protected bacteria less capable of adhering to a substratum. Again, the method is effected by subjecting the surface protected bacteria to a glycosaminoglycans degrading enzyme.

Further in accordance with the teachings of the present invention there is provided a method of treating a disease for relieving disease associated symptoms effected by the administration a therapeutical composition including a glycosaminoglycans degrading enzyme.

According to still another aspect of the present invention there is provided a therapeutic composition for treating a surface protected bacteria associated disease or symptoms. The comprising a glycosaminoglycans degrading enzyme and an antibiotic. Examples of antibiotics are given in the Examples section hereinunder.

According to yet another aspect of the present invention there is provided a bactericide composition effective in eliminating a surface protected bacteria. The bactericide composition includes a glycosaminoglycans degrading enzyme and a bactericide.

As used herein, the term "glycosaminoglycans" refers to polysaccharide-protein conjugates, such as, but not limited to, heparan sulfate, hyaluronic acid, chondroitin sulfate, keratan sulfate I, II, dermatan sulfate and heparin.

As used herein in the specification and in the claims section below, the term "surface protected bacteria" refers to mucoid bacteria, alginate-producing bacteria and/or biofilm-producing bacteria.

As used herein in the specification and in the claims section below, the term "anti-bacterial agent" refers to natural and man-made agents effective in killing and/or inhibiting the growth rate of bacteria. Anti-bacterial agents according to the present invention include bactericides, such as, but not limited to, biocide SDS, antibiotics and immune moieties, such as antibodies and immune cells, e.g., macrophages, T cells and the like.

The glycosaminoglycans degrading enzyme according to the present invention can be of any type. It can be a lysosomal hydrolase or a bacterial lyase. It can be an endoglycosidase, an exoglycosidase or a sulfatase. It can, for example, be any one or combination of the following enzymes: heparanse, connective tissue activating peptide III (CTAP), hyaluronidase, glucoronidase, iduronate sulfatase, heparinase I, heparinase II heparinase III, chondroitinase ABC, chondroitinase AC, chondroitinase B and/or chondroitinase C.

The surface-protected bacteria according to the present invention can be of any genus capable of surface protection, including, but not limited to, Pseudomonas, Azotobacter, Azomonas, Serpens, Fusobacterium, Klebsiella, Streptococcus, Staphylococcus or Treponema. *Pseudomonas aeruginosa* which is known to cause pulmonary infection in CF patients is of particular interest.

Thus, the method and composition according to the present invention is effective in treating lungs of patients suffering chronic pulmonary infection, associated, for example, with cystic fibrosis, for relieving symptoms associated therewith. Treating infected lungs according to the present invention is preferably effected by an inhaler device designed to generate an aerosol of the therapeutic composition according to the present invention. Yet, the present invention is also effective in treating other organs of the body and/or other conditions, such as, but not limited to, ears, eyes, teeth, gums, wounds and burns which can be infected by surface protected bacteria.

As used herein in the specification and in the claims section below, the term "treating" when used in conjunction with a disease refers to substantially inhibiting, slowing or reversing the progression of a disease, substantially ameliorating clinical symptoms of a disease or substantially preventing the appearance of clinical symptoms of a disease.

For therapeutic and/or prophylactic treatment, the glycosaminoglycans degrading enzyme according to the present invention can be formulated in a composition, which may include thickeners, carriers, buffers, diluents, surface active agents, preservatives, and the like, all as well known in the art. Pharmaceutical compositions may also include one or more active ingredients such as but not limited to anti inflammatory agents, anti microbial agents, anesthetics, bactericides, antibiotics and the like in addition to the glycosaminoglycans degrading enzyme. Other enzymes, such as DNase can also be included for some applications (e.g., treatment of CF lung).

The pharmaceutical composition can be administered in either one or more of ways depending on whether local or systemic treatment is of choice, and on the area to be treated. Administration may be done topically (including ophtalmically, vaginally, rectally, intranasally), orally, by inhalation or parenterally.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Formulations for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include but are not limited to sterile aqueous solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons ordinarily skilled in the art can easily determine optimum dosages, dosing methodologies and repetition rates.

The method and bactericide composition according to the present invention are effective in inhibiting or killing surface protected bacteria growing on a non-living substratum, which forms, for example, a part of a medical device, such as, but not limited to, infusion device, a catheter device, a contact lens device, a dialysis device and a draining device.

The present invention successfully addresses the shortcomings of the presently known configurations by providing new means to combat surface protected bacteria (e.g., mucoid-, alginate-, biofilm-producing bacteria), which is effected by subjecting such bacteria to GAG degrading enzyme, rendering such bacteria surface non-protected and susceptible to anti-bacterial agents and less capable of adhering to various substrata.

Thus, according to the present invention glycosaminoglycans degrading enzymes, such as, but not limited to, heparanases, connective tissue activating peptide, heparinases, glucoronidases, heparitinases, hyaluronidases, sulfatases and chondroitinases are used, alone, in combination, or in combination with conventional substances, preferably as aerosol, for the management of diseases associated with infection by surface protected bacteria.

The effects of glycosaminoglycans degrading enzymes on the amounts of bacterial alginate production and the associated payoffs, in addition to their effects on reducing the viscosity of sinuses and airway secretions with associated implications derived from cellular heparan sulfate degradation on curtailing the rate of infection and inflammatory responses (see U.S. patent application Ser. No. 09/046,475), will result in reduction and/or prevention of chronic infection, reduction of tissue damage, thus improving the patients quality of life and prolong life span.

Each of the various embodiments and aspects of the present invention as delineated hereinabove and as claimed in the claims section below finds experimental support in the Examples section that follows.

EXAMPLES

Reference is now made to the following examples, which together with the above descriptions, illustrate the invention in a non limiting fashion.

Materials and Experimental Methods

Bacterial strain: Clinical isolates of a mucoid *Pseudomonas aeruginosa* strains from CF patients were kindly provided by Dr. H Berkovier from the Hadassa hospital, Ein Kerem, and Prof. E. Kerem from Shaarei Tsedek hospital, Jerusalem. Bacteria were grown on either McConkey agar plates (Hi Labs, Israel), or tryptic soy broth (TSB)+1.5% agar (Difco) or 1.5% agarose (FMC BioProducts, USA) plates, or in tryptic soy broth (Difco Laboratories, USA).

Monosaccharide composition of *P. aeruginosa* alginate: Monosaccharide composition of *P. aeruginosa* alginate was tested using FACE Glycosaminoglycan Identification Kit (Glyco, Inc., Novato, Calif., USA), according to manufacture's instructions.

Reduction of Alginate

1. TSB+1.5% agar or 1.5% agarose plates were prepared according to manufactures instructions. Plates were covered with mucoid *P. aeruginosa* isolate using a cotton swab. Whatman's 25 mm 3MM discs were then placed on the seeded bacteria. The discs were loaded with either 50 $\mu$l 0.1 $\mu$g/$\mu$l recombinant human heparanase, or 50 $\mu$l 0.1 $\mu$g/$\mu$l heat inactivated (10 min at 100° C.) recombinant human heparanase, or 50 $\mu$l heparanase buffer (10 mM buffer phosphate pH 6.8, 0.4 M NaCl, with or without 1 mM DTT), or 25 $\mu$l (3 units/$\mu$l) hyaluronidase (Sigma), or 25 $\mu$l heparinase II (0.01 unit/$\mu$l) (kindly provided by Prof I. Vlodavsky of the Hebrew University of Jerusalem)+25 $\mu$l saline, or 25 $\mu$l (1 unit /$\mu$l) DNase (Promega)+25 $\mu$l saline, or 25 $\mu$l (0.01 u/$\mu$l) chondroitinase ABC (Sigma)+25 $\mu$l saline. The plates were incubated at 37° C. for 18 hours. The disc's surfaces were examined for the presence of mucus. Then, each disc was tapped with a bacterial needle and the bacteria were cultured 18 hours at 37° C. on TS agar plates. The phenotype of the colonies was observed and further tested for sensitivity to antibiotics.

2. A bacterial colony was collected with a sterile tip and suspended in 500 $\mu$l saline. Fifty $\mu$l were added to a culture medium containing 50% TSB, 50% saline, 20 mM citrate-phosphate buffer pH 5.6 with either heparanase 2.5 $\mu$g/ml (50 $\mu$l), or 50 $\mu$l boiled heparanase, or 50 $\mu$l heparanase buffer. Culture was shaken 18 hours at 37° C. A sample from each tube was recultured on a TS agar plate and incubated at 37° C., 18 hours, and the cultures phenotype was recorded. 0.5 ml from each tube was sampled for viscosity testing, using microviscosometer (Haake, W. Germany).

Resistance of Mucoid vs. Nonmucoid Bacteria

Antibiotic susceptibility test discs: The enzyme-treated discs were tapped with a cotton swab that was then used to seed the "treated" bacteria onto a new TS plate. Susceptibility discs were then placed on the seeded plates and incubated for 18 hours at 37° C. The zone of inhibition of bacterial growth was measured with a ruler.

MIC: The minimal inhibitory concentration (MIC) was determined by serial dilutions of various types of antibiotics (Enrofloxacin, sulfa/trimethoprim, gentamycin and amikacin), for various *P. aeruginosa* isolates obtained.

The effect of a combined treatment (enzyme and antibiotics) at either MIC or MIC-1, or the treatment with the enzyme followed by the antibacterial treatment at MIC, MIC-1 or MIC-2, on the number of bacteria grown was assessed by O.D. readings at 630 nm.

EXPERIMENTAL RESULTS

Figure 1:
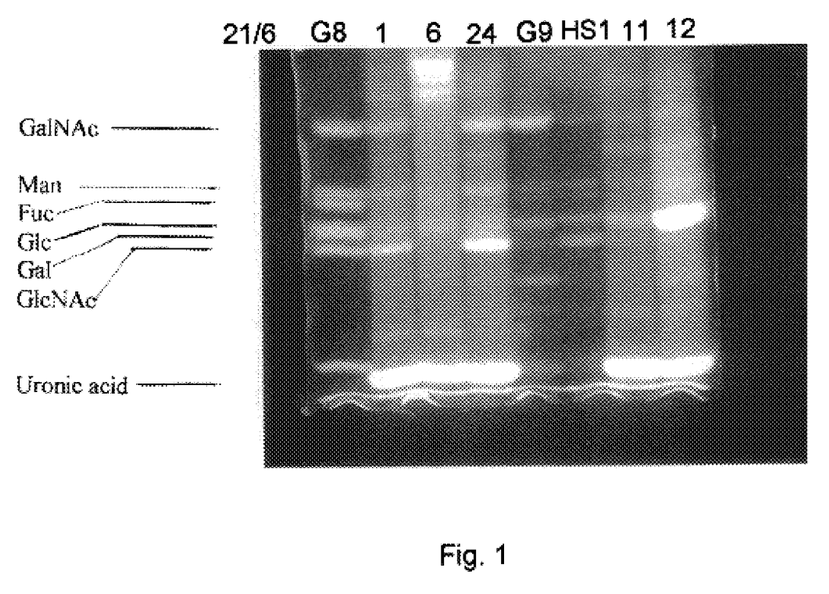
FIG. 1 demonstrates the monosaccharide composition of mucoid *P. aeruginosa* isolate No. 1 (samples 11, 12) and of three sputum samples from CF patients (samples 1, 6, 24), as well as of heparan sulphate standard (HS1), chondroitin sulfate A (G9), and of monosaccharide standard ladder (G8).
Figure 2A:
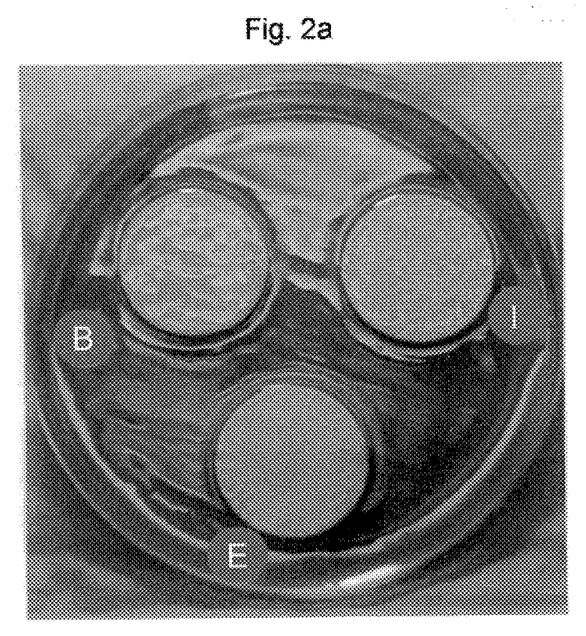
FIGS. 2a–e demonstrate the effect of heparanase on the amount of mucus produced by mucoid *P. aeruginosa* isolate No. 1. Bacteria were plated on tryptic soy agar (2a–d) or McConkey agar (2e). Discs soaked with the examined compound were placed on top. E=heparanase, I=boiled heparanase, B=heparanase buffer, C=chondroitinase ABC, C-I=boiled chondroitinase, D=DNase, D-I=boiled Dnase, Hy=hyaluronidase, H-II=heparinase II.
Figure 2B:
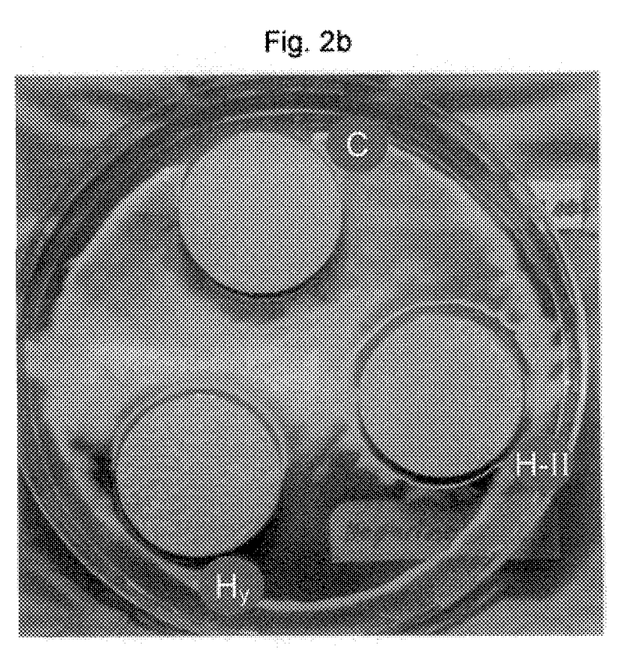
Figure 2C:
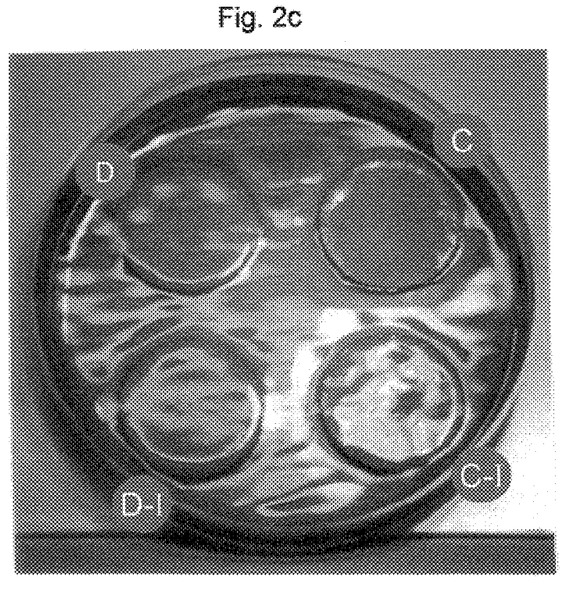
Figure 2D:
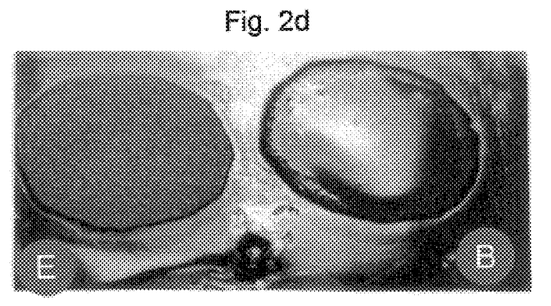
Figure 2E:
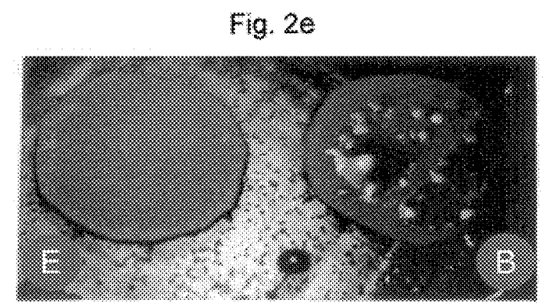

In an attempt to elucidate the composition of the alginate, and find whether it has the characteristics of glycosaminoglycans making it a substrate for GAG degrading enzymes, mucoid *P. aeruginosa* isolate No. 1 were collected, and analyzed using the GAG identification kit. The results, which are shown in FIG. 1, indicate that the alginate has amino sugars and uronic acid and galactose, which compose the disaccharides units of the GAG.

Figure 3A:
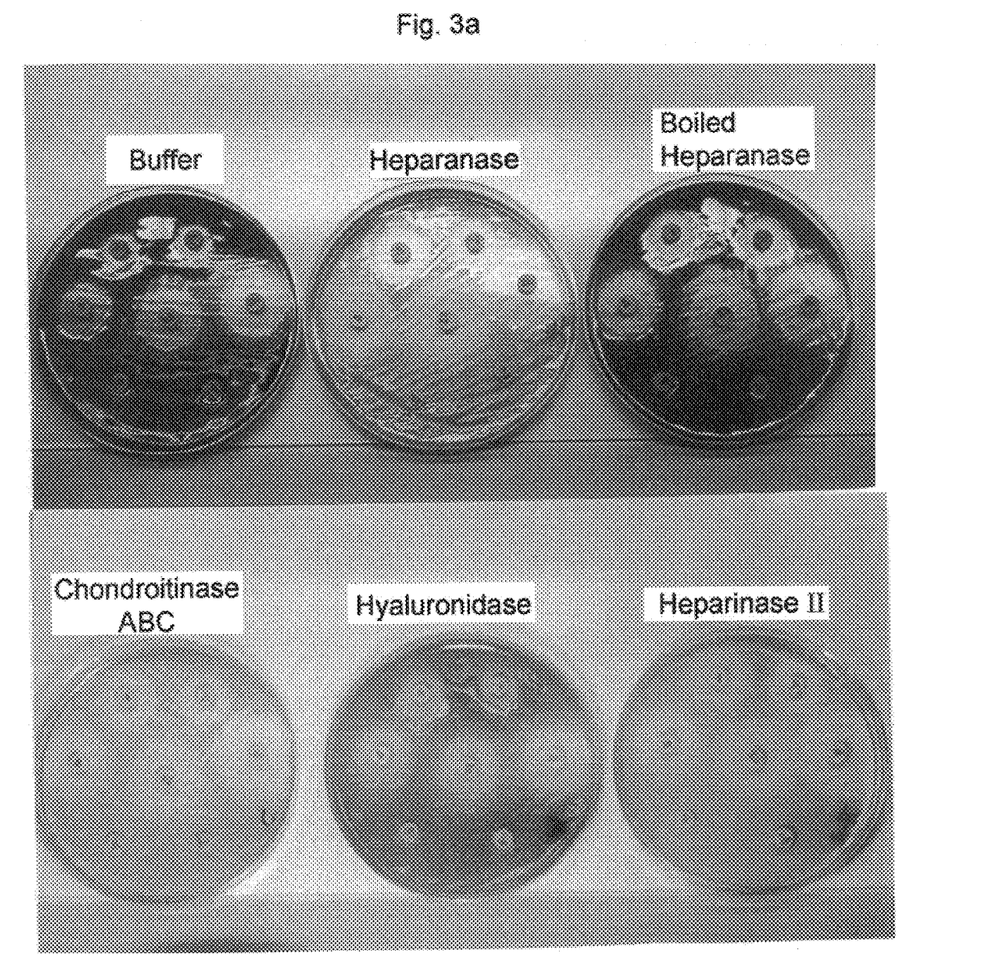
Figure 3B:
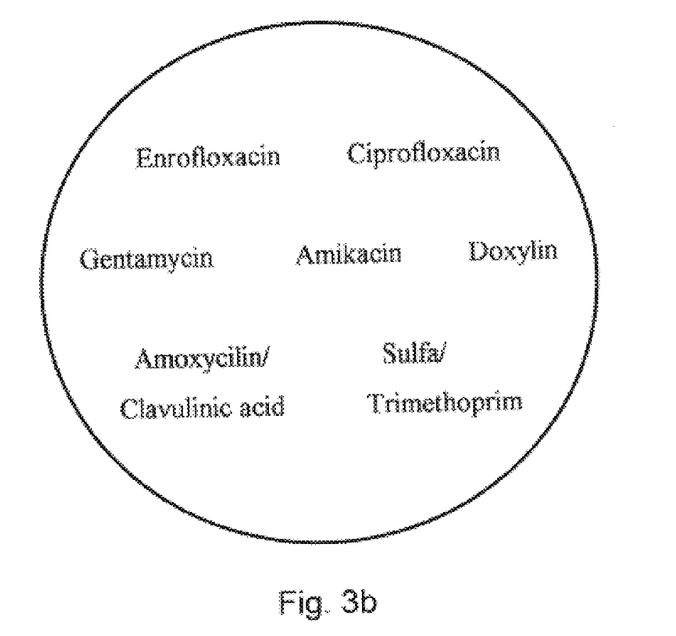
Figure 4A:
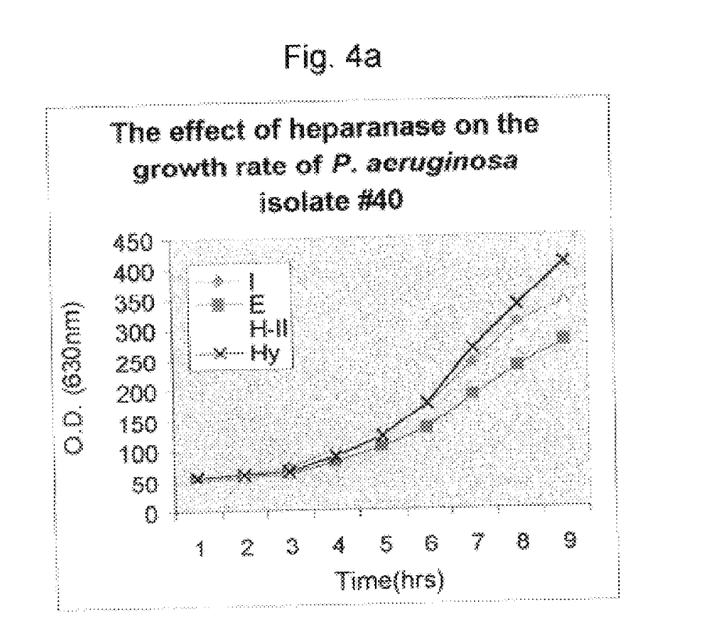
FIGS. 4a–e demonstrate the effect of heparanase on mucoid *P. aeruginosa* isolate No. 40 proliferation rate and sensitivity to antibiotics. (4a) The proliferation rate following treatment with I=boiled heparanase, E=heparanase, H-II=heparinase II, Hy=hyaluronidase. (4b–e) The proliferation rate as in FIG. 4a, in the presence of antibiotics, (4b) amikacin at MIC-2 (0.78 µg/ml); (4c) amikacin at MIC-1 (1.56 µg/ml); (4d) gentamycin at MIC-2 (0.39 µg/ml); (4e) gentamycin at MIC-1 (0.78 µg/ml).
Figure 4B:
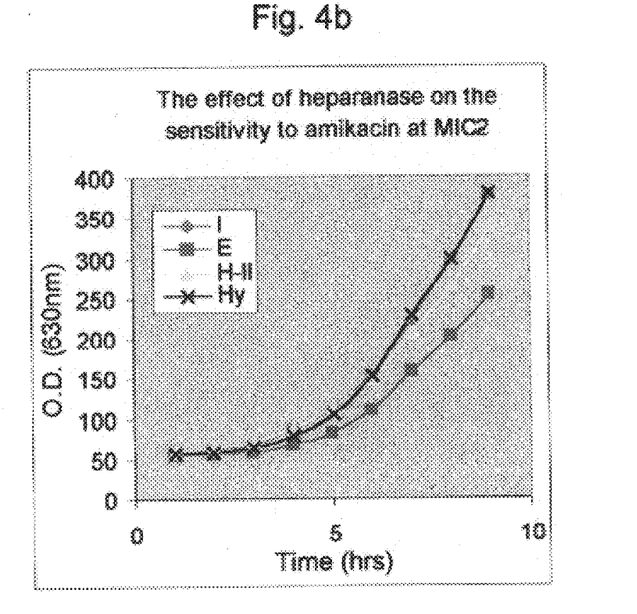
Figure 4C:
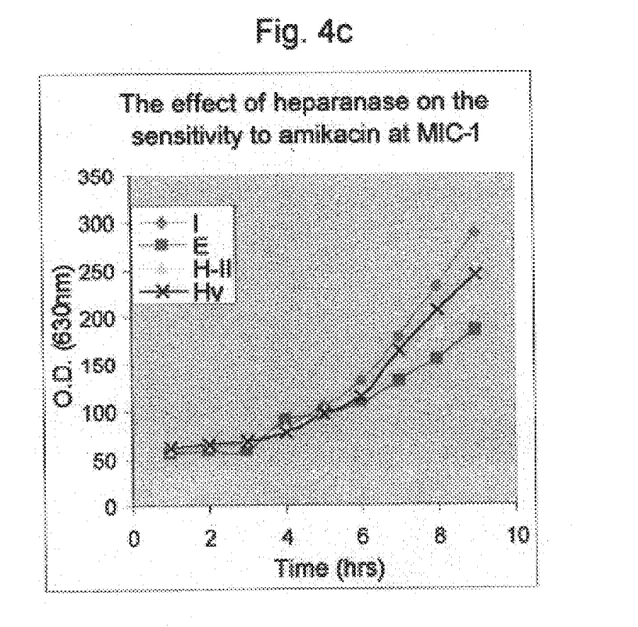
Figure 4D:
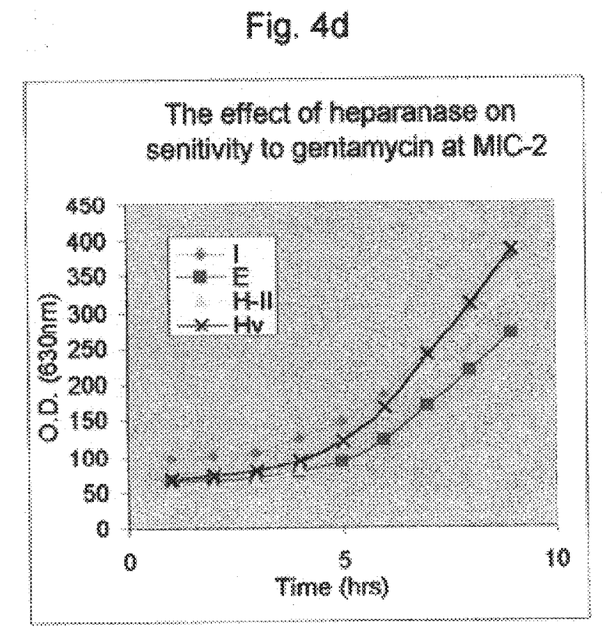
Figure 4E:
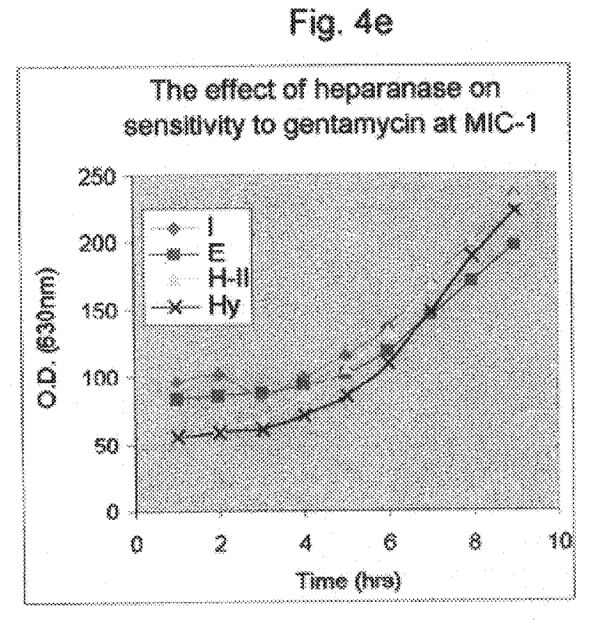

In order to test the possibility that GAG degrading enzymes may reduce the amount of mucoid bacteria or reduce the amount of alginate, Watmann's 3MM disc were used following the concept of susceptibility discs. The discs were placed on a TS agar plate that was previously seeded with *P. aeruginosa* isolate No. 1. The results, which are shown in FIGS. 2a–e, demonstrate that discs soaked with heparanase, heparinase II and chondroitinase ABC had a dry appearance, while discs soaked with hyaluronidase, DNase, buffer, boiled heparanase and DNase were covered with mucus and had a shiny appearance. Tapping the center of each disc, and replating, revealed that the discs were contaminated by live mucoid *P. aeruginosa*, (not shown). After the addition of 50 $\mu$l of gentamycin at MIC-2 (3.15 $\mu$g/ml, MIC=12.5 $\mu$g/ml) to the center of each disc and incubating for 5 hours, the center of each disc was tapped with a cotton swab and the bacteria were seeded on TS plates. A variety of susceptibility discs were then placed on the seeded plates and incubated for 18 hours at 37° C. The results, which are presented in FIGS. 3a–b and Table 1 below, reveal that the bacteria that were treated by heparanase, heparinase II and chondroitinase ABC followed by gentamycin at MIC-1, were more susceptible to 5 of 7 antibiotics tested and produced less alginate, as is compared to the bacteria treated by hyaluronidase, buffer and boiled heparanase.

TABLE 1

| Diameter (mm) of bacterial growth inhibition | | | | | | |
|---|---|---|---|---|---|---|
| | E | I | B | Hy | H-II | C |
| Amikacin | 26 | 23 | 22 | 21 | 24 | 25 |
| Doxylin | 29 | 24 | 19 | 22 | 27 | 27 |
| Ciproflox | 18 | 15 | 13 | 12 | 18 | 17 |
| Enroflox | 21 | 15 | 13 | 14 | 18 | 21 |
| Gentam | 23 | 19 | 17 | 17 | 21 | 23 |
| SxT | ns | ns | ns | ns | ns | ns |
| Amox/Cla | ns | ns | ns | ns | ns | ns |

E = heparanase, I = boiled heparanase, B = heparanase buffer, Hy = hyaluronidase, H-II = heparinase II, C = chondroitinase ABC, ns = not sensitive.

In order to further establish the supposition that heparanase may induce changes in alginate producing bacterial count, changes in the total amount of alginate, and alterations in sensitivity to antibiotics, *P. aeruginosa* (isolate No. 40) was seeded on a TS agar plate. 3MM discs soaked with either heparanase, boiled heparanase, heparanase-buffer, hyaluronidase or heparinase II were placed on top. After 18 hours of incubation at 37° C., the discs that were treated with heparanase, boiled heparanase, heparanase buffer and heparinase-II had a dry appearance, and the disc that was treated with hyaluronidase had a shiny appearance. This bacterial isolate produced less alginate in general and was more sensitive to antibiotics (Table 2). The disks that were soaked with either heparanase, boiled heparanase, heparinase II or hyaloronidase were then washed in 50 ml tubes containing TSB. The bacteria containing broth was further diluted and divided into 96 well plates with various antibiotics at different concentrations (MIC-1, MIC-2). The results, which are summarized in FIGS. 4a–e, show that the proliferation rate of bacteria treated previously with heparanase or heparinase II is slower compared to bacteria treated with boiled heparanase or hyaluronidase.

TABLE 2

Minimal inhibitory concentration

| Isolate No. | Gentamycin | Enrofloxacin | Amikacin |
|---|---|---|---|
| No. 1 | 12.5 | 6.25 | 25 |
| No. 38 | 12.5 | 6.25 | nd |
| No. 39 | 3.12 | 0.78 | nd |
| No. 40 | 1.56 | 3.12 | 3.12 |
| No. 41 | 0.78 | 1.56 | nd | nd = not determined

Thus, heparanase, heparinase II and chondroitinase ABC, all of which are GAG degrading enzymes, induce phenotypic changes of mucoid *P. aeruginosa*, exhibiting a reduced amount of alginate, slower proliferation rate and higher susceptibility to a wide range of antibiotics. The mechanism by which these enzymes induce these changes is still under investigation, yet several possible mechanisms are postulated herein in a non-limiting fashion (i) the enzymes degrade the alginate; (ii) the enzymes interfere with alginate production; (iii) the enzymes interfere with intercellular signaling for alginate production or alginate degradation by lyases; (iv) the enzymes inhibit bacterial proliferation.

Although the invention has been described in conjunction with specific embodiments thereof, it is evident that many alternatives, modifications and variations will be apparent to those skilled in the art. modifications and variations will be apparent to those skilled in the art. Accordingly, it is intended to embrace all such alternatives, modifications and variations that fall within the spirit and broad scope of the appended claims.

What is claimed is:

1. A method of rendering a surface protected Pseudomonas bacteria more susceptible to an anti-bacterial agent comprising the step of subjecting said Pseudomonas bacteria to a heparanase enzyme.

* * * * *